United States Patent [19]
Poole et al.

[11] Patent Number: 5,453,380
[45] Date of Patent: Sep. 26, 1995

[54] THIN FILM SAMPLE PREPARATION

[75] Inventors: John S. Poole, Elkton, Md.; Mark A. Nickerson, Landenberg; Frank J. DeMonte, West Chester, both of Pa.

[73] Assignee: Hewlett-Packard Company, Palo Alto, Calif.

[21] Appl. No.: 198,724

[22] Filed: Feb. 18, 1994

[51] Int. Cl.[6] .................................................. G01N 1/28
[52] U.S. Cl. ...................... 436/174; 436/178; 436/180
[58] Field of Search ................................... 436/174–178, 436/179, 180

[56] References Cited

U.S. PATENT DOCUMENTS 3,966,410  6/1976  Jahnsen .......................... 23/230 B
4,017,597  4/1977  Reynolds ......................... 424/1.5
4,425,320  1/1984  Perry et al. ...................... 424/1.1

Primary Examiner—David A. Redding
Attorney, Agent, or Firm—Richard F. Schuette

[57] ABSTRACT

A method for sample preparation in which a sample matrix is formed into a thin film prior to being brought into contact with an extraction solvent such that the surface area contact between the sample matrix and the solvent is maximized and the cross section of the sample matrix and corresponding diffusion path of components of interest is minimized.

14 Claims, 8 Drawing Sheets

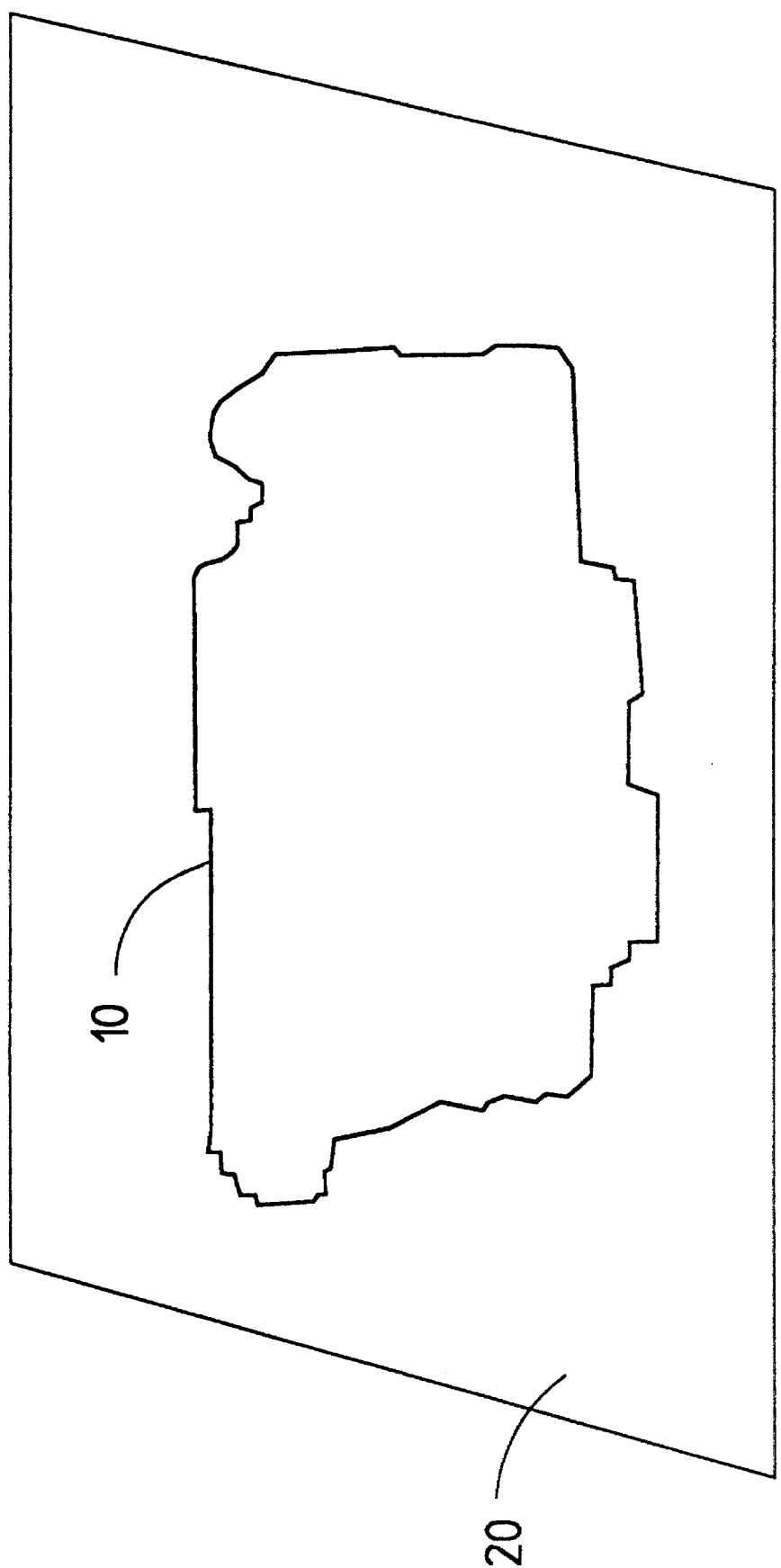

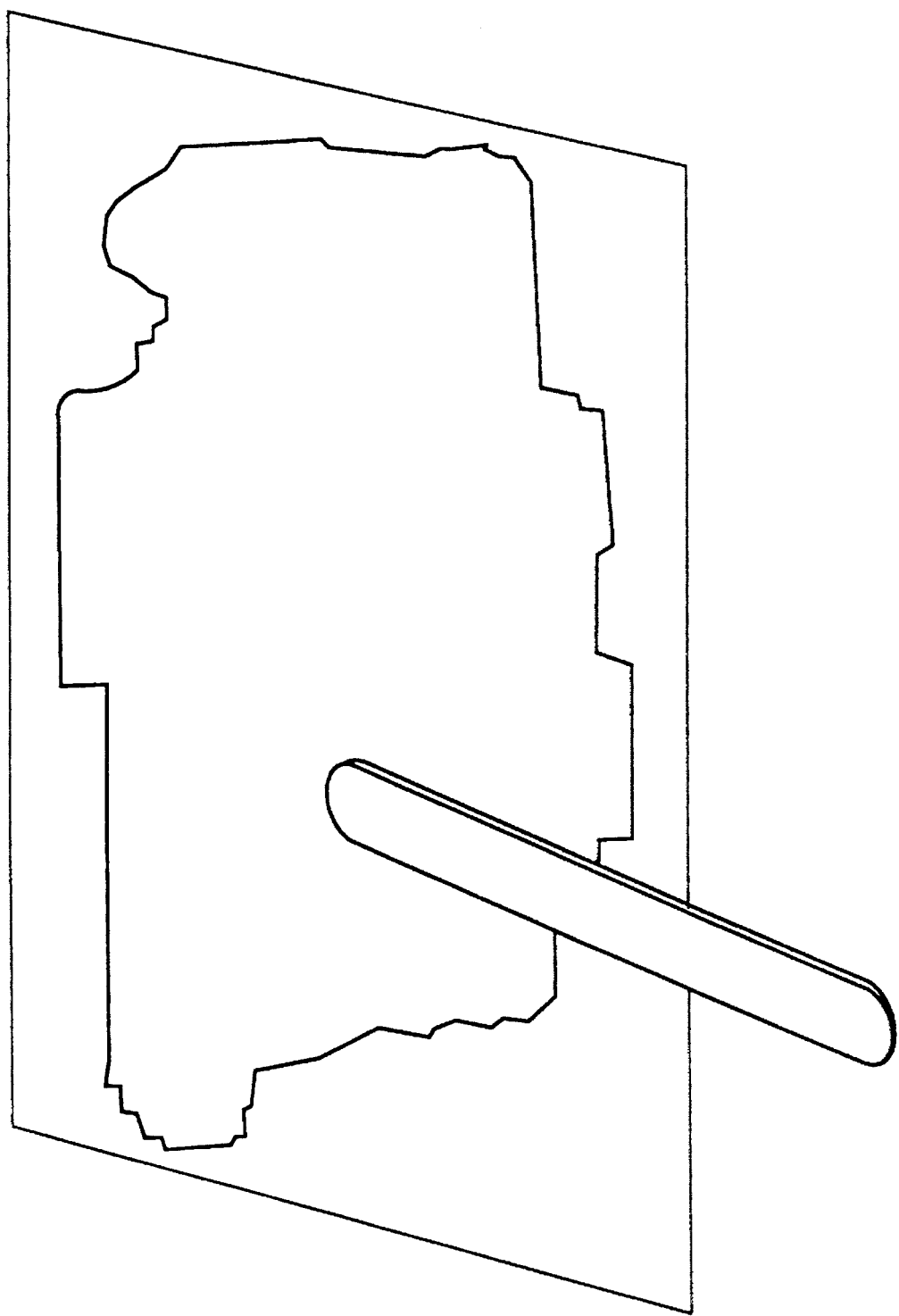

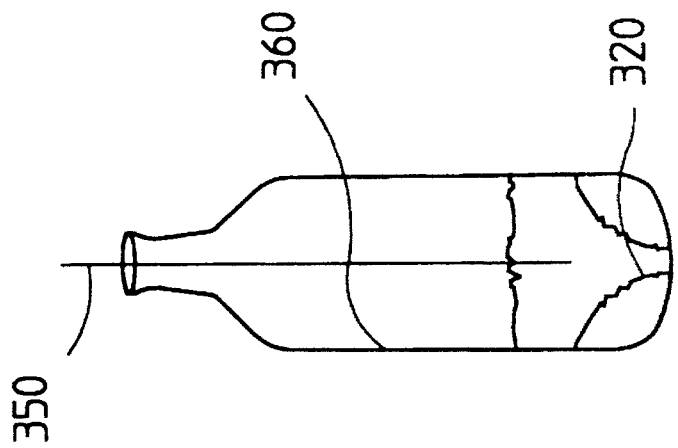
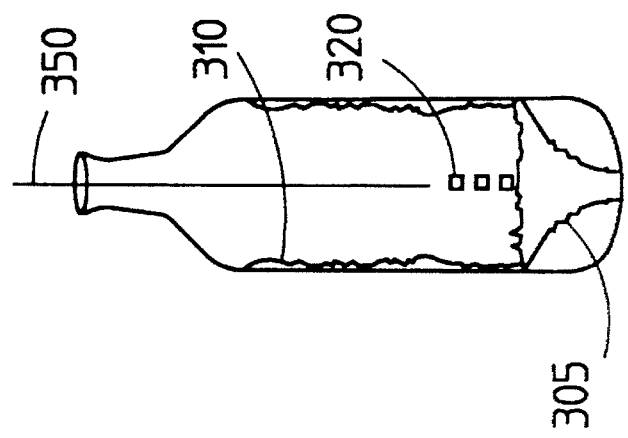
FIG 3C
FIG 3B
FIG 3A

THIN FILM SAMPLE PREPARATION

FIELD OF THE INVENTION

The invention provides for enhanced extraction of components of interest from a sample matrix by an extraction solvent. The sample matrix is formed into a thin film to optimize surface contact between the sample matrix and the extraction solvent and at the same time minimizes the cross section of the sample matrix, thus minimizing the distance through which the extraction solvent must diffuse in order to dissolve the components of interest.

BACKGROUND OF THE INVENTION

Extraction is defined as a chemical or physical process for drawing out components of interest from a sample matrix. Traditional means of extraction involve mixing an extraction solvent with the sample matrix such that components of interest dissolve into the solvent in an attempt to achieve equilibrium based on the relative solubility of the sample matrix and the solvent. Solvent containing dissolved components can then be aspirated or otherwise removed for detection by a spectrographic device or injection into a chromatographic device.

Thorough mixing of the sample matrix and the solvent is important to maximize the contact between the sample matrix and the solvent. A number of improved methods for mixing include mechanical agitation, ultrasonic dissociation, shaking or stirring. Additionally, heating is sometimes employed to assist in the release of the components of interest. Depending on the complexity of the sample matrix undergoing extraction, it may take from several hours to several days to complete an extraction. The amount of a desired component extracted is dependent upon many variables including the extraction method used, complexity of the sample matrix and degree of mixing.

SUMMARY OF THE INVENTION

The invention provides for enhancing the speed and precision of extracting components of interest from a solid, liquid or a suspension/emulsion sample matrix. The sample matrix is formed into a thin, uniform film so as to maximize the surface area for a given sample volume. Maximizing the surface area in contact with the solvent increases the rate at which the components of interest come into equilibrium between the sample matrix and the solvent. Formation of a thin, uniform film also ensures that the cross section of the sample matrix is minimized so as to minimize the distance through which the extraction solvent must diffuse in order to dissolve the components of interest.

Manually spreading the sample matrix onto a support medium provides for the formation of a thin, uniform film. The substrate and sample matrix can then be loosely coiled and placed within a sample vial for further processing with an extraction solvent.

The invention may also be automated to provide a thin, uniform film on the inside walls of a sample container. In particular, a sample matrix is placed in a sample container or sample vial which is then rotated about its vertical axis at a rate dependent upon the viscosity of the sample matrix. Centrifugal force causes the sample matrix to form into a thin film on the inside walls. This action may also be construed as vortexing the sample. Solvent is then introduced into the sample vial to wash the sample. The amount of solvent required to wash the sample can be minimized by rotating the sample vial such that centrifugal force causes the solvent to form a thin layer over the sample matrix.

Thin Film Sample Preparation may also include the step of forming, on the inside surface of a sample container, a thin film of a compound having an affinity for components of interest or an affinity for contaminants in the sample matrix. One or more solvents can then be used to wash and or extract components of interest from the sample matrix. In another embodiment, a desiccant coating is formed on the inside surface of the sample vial by rotating about the vertical axis. A sample is then dried by introducing the sample into the vial and rotating the sample vial to ensure maximum contact between the sample and the desiccant coating.

The invention may also be employed for headspace extractions where gaseous solvents are utilized. In particular, a sample vial is rotated at a rate to form the sample matrix into a thin film on the inside walls. The sample matrix is then heated in the presence of a gaseous extracting solvent such that the components of interest are allowed to come into equilibrium in the gas phase. Forming the sample matrix into a thin film minimizes the distance the volatile components must diffuse through to establish equilibrium. Inserting a dispense needle into the central region of the sample vial provides for aspiration of a portion of the gaseous extracting solvent for analysis. Forming the sample into a thin film insures that equilibrium occurs much faster and is more uniform than if the sample were in a more conventional shape. Where the sample matrix is a liquid, or some other form which will not maintain the thin film shape after rotation, the rotating operation can be continued while the surface of the sample matrix is washed with a solvent or purged with a gas.

BRIEF DESCRIPTION OF THE DRAWINGS

FIG. 1A is a perspective view of a preferred embodiment of the invention in which a sample matrix is placed upon a flat support medium.

FIG. 1B is a perspective view of a preferred embodiment of the invention in which the sample matrix is manually spread into a thin uniform layer.

FIGS. 3A–3C are a perspective view of another embodiment of the invention in which the sample is dried in a rotating sample vial having a desiccant coating.

DESCRIPTION OF THE PREFERRED EMBODIMENT

Figure 1D:
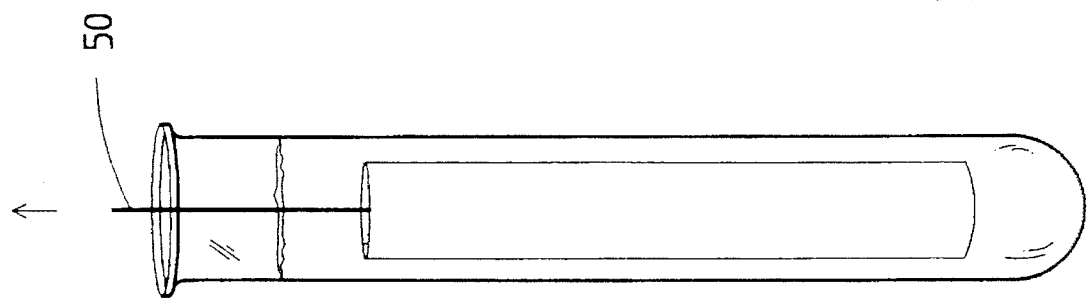
FIG. 1D is a perspective view of a preferred embodiment of the invention in which the solvent introduced into the sample vial illustrated in FIG. 1C is aspirated.
Figure 1C:
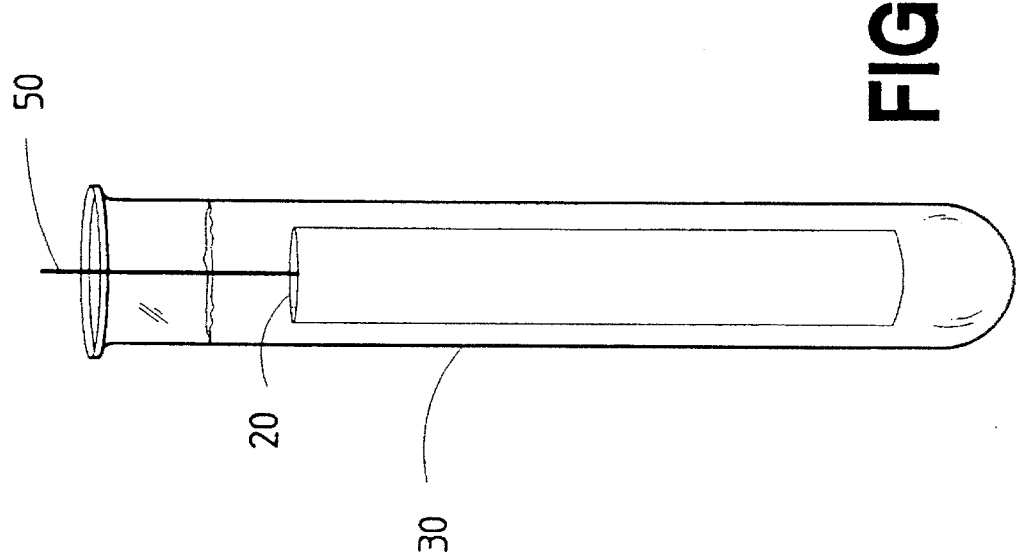
FIG. 1C is a perspective view of a preferred embodiment of the invention in which the support medium illustrated in FIG. 1A is rolled up and placed in a sample vial to which solvent is added.

FIG. 1 illustrates a method in which a sample matrix 10 is spread into a thin film on support medium 20. Support medium 20 is then loosely coiled such that it can be placed in a sample vial 30. Needle 50 is employed for introducing an extraction solvent such as hexane or methylene chloride. Since the cross section of the sample matrix is relatively small in relationship to its surface area, the rate at which the components of interest come into equilibrium between the sample matrix and the solvent is relatively fast. Additionally, the uniformity of the sample matrix provides for accurate and reproducible results. Once the components of interest have dissolved into the extraction solvent, needle 50 is employed is employed for aspirating the solvent.

Figure 2C:
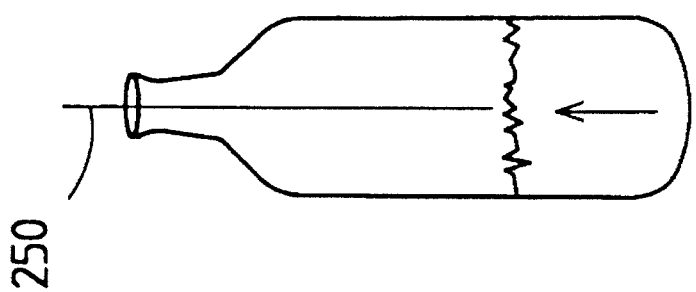
FIGS. 2A–2C are a perspective view of a preferred embodiment of the invention in which a sample vial is rotated to force the sample matrix into a thin, uniform film.
Figure 2B:
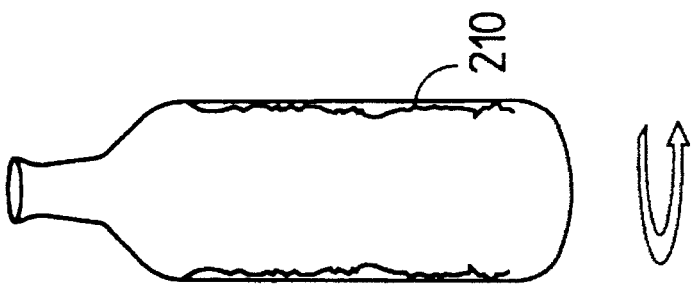
Figure 2A:
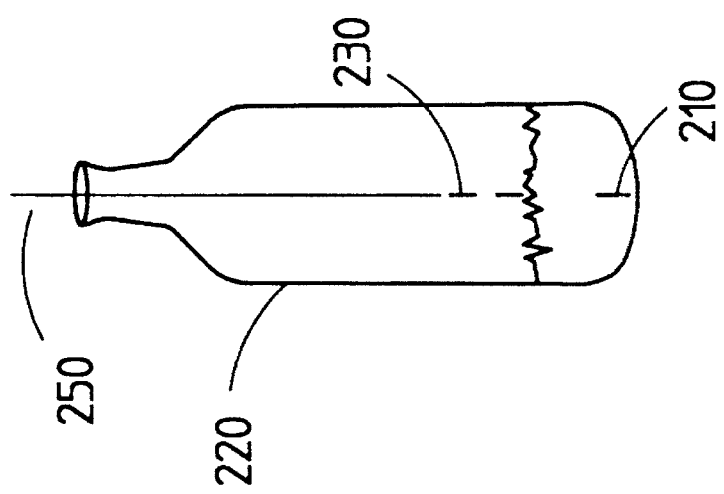

FIG. 2 illustrates another embodiment of the invention in which the sample matrix 210 is placed in a sample container or sample vial 220 and rotated at speeds such that centrifugal force causes the sample matrix to form as a thin film on the inside surface of the sample vial. A typical speed range is 500 rpm to 10,000 rpm depending on the viscosity of the sample matrix. A small amount of extraction solvent 230 (approximately 5%–40% of the sample vial volume, ie., for a standard 2 ml sample vial, 0.1 ml–0.8 ml) is then introduced. The sample vial is then rotated such that the extraction solvent is forced into contact with the sample matrix on inside surface of the sample vial. Once extraction is completed, rotation of the sample vial is stopped, the needle 250 is reinserted into the sample vial and the extraction solvent containing the components of interest is aspirated. The amount of solvent required for extraction can be reduced further using a sample vial having a conical bottom portion 305 designed for maximum retrieval as set forth in FIG. 3. This invention is particularly advantageous as it results in a highly concentrated, small volume of extraction solvent for analysis by standard chromatographic methods.

FIG. 3 illustrates another embodiment of the invention in which it is employed for drying a sample matrix. A thin film of desiccant coating 310 is formed on the inside surface of a sample vial by rotating the sample vial at a high rate of speed. A needle 350 is employed for dispensing sample matrix 320 into the sample vial. The sample vial is then rotated to ensure complete contact between the sample matrix and the desiccant coating. Moisture 360 binds with the desiccant coating to effectively "dry" out the sample matrix. The needle 350 is then reinserted for aspirating the sample out of the sample vial for analysis.

Figure 4C:
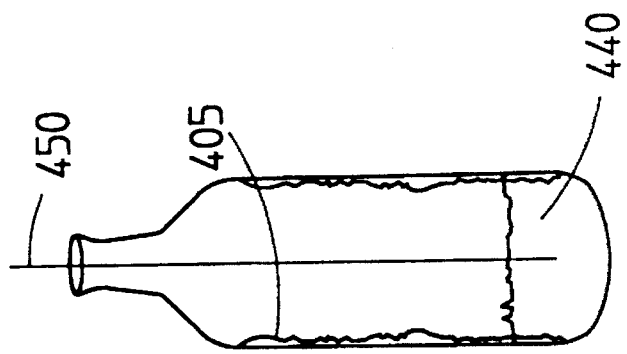
FIGS. 4A–4C are a perspective view of another embodiment of the invention in which a contaminant in a sample is separated from the sample by rotating the sample in a sample vial having an inner coating with an affinity for the contaminant.
Figure 4B:
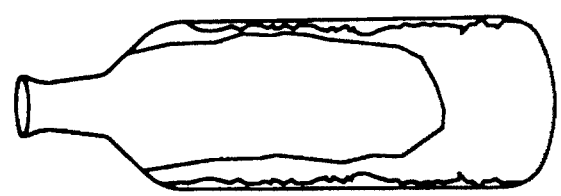
Figure 4A:
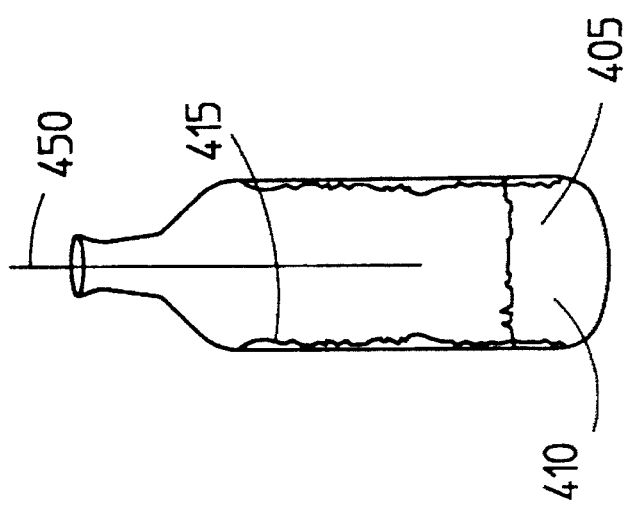
Figure 5C:
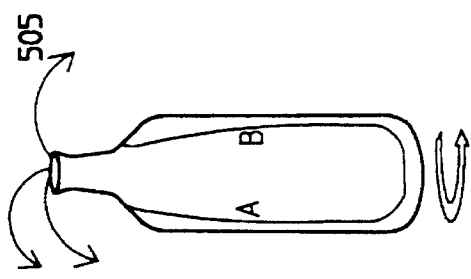
FIG. 5A–5E are a perspective view of another embodiment of the invention in which two compounds are separated.
Figure 5B:
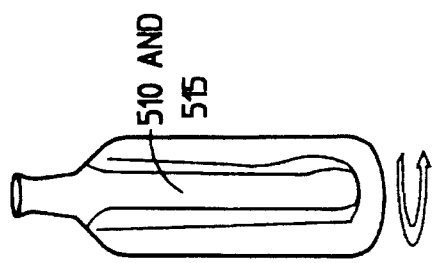
Figure 5E:
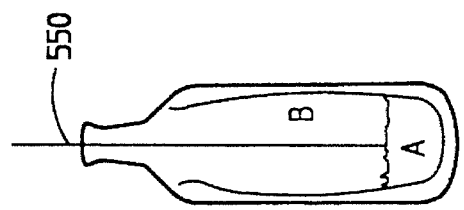
Figure 5A:
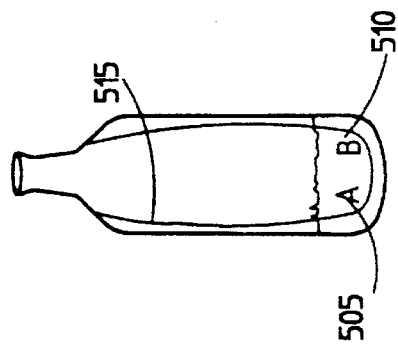
Figure 5D:
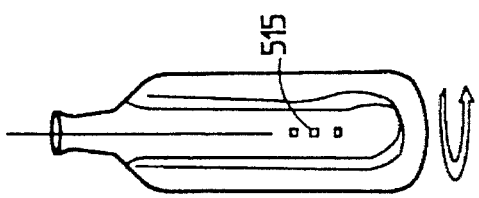

FIG. 4 illustrates the invention employed for removing contaminants 405 from a sample matrix 410. The inner surface of a sample vial is first treated with a coating 415 having an affinity for a known contaminant that an analyst desires to remove from the sample matrix prior to analysis. The sample vial can be rotated to ensure that the coating 415 is in a thin film. The sample matrix 410 is introduced into the sample vial by needle 450 and then forced into contact with the coated sample vial by centrifugal force. The containments 405 are retained by the coating 415 on the inner surface of the sample vial such that the pure sample 440 can be aspirated by the needle 450.

FIG. 5 illustrates the invention in which the inner surface of a sample vial is first treated with a coating 515. A sample matrix 510 having components A and B in solution with a solvent 505 is placed into the sample vial by a needle 550 and is rotated at a first relatively slow speed such that the sample matrix 510 adheres to the coating 515. The sample vial is then rotated at a relatively high speed to evaporate the first solvent 505. A second solvent 525 is then added to the sample vial to dissolve component A while leaving component B adhered to the inner wall of the sample container. Needle 550 is then employed for aspirating component A from the sample vial for analysis.

Figure 6C:
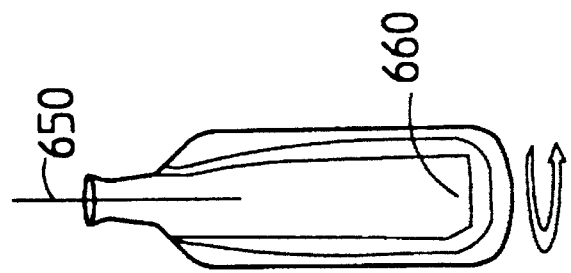
FIGS. 6A–6C are a perspective view of another embodiment of the invention in which headspace extraction is performed.
Figure 6B:
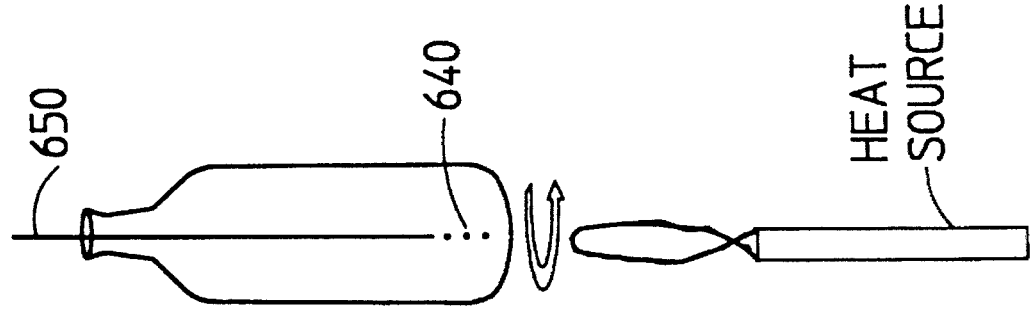
Figure 6A:
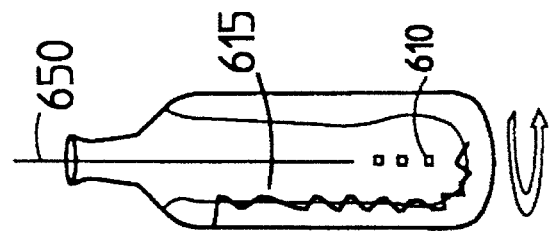

FIG. 6 illustrates how the invention may be employed for headspace extractions where gaseous solvents are utilized. In particular, a dispense needle 650 is employed for inserting sample matrix 610 into sample vial 600. The sample vial is then rotated at a fast rate such that sample matrix 610 is formed into a thin film 615 on the inside walls of the sample vial. The dispense needle 650 adds a volatile extraction solvent 640 which may be in the form of a liquid or a gas. The sample matrix is then heated in the presence of the extracting solvent 640 such that the components of interest are allowed to come into equilibrium in the gas phase within the sample vial. If components of interest are relatively volatile, heating may not be required. The dispense needle 650 may now be employed for aspirating the headspace 660 to retrieve the volatile components of interest from the headspace within the sample vial. Additionally, the sample vial may be rotated such that the heavier components of the matrix are forced outward and the lighter volatile components of interest move to the center of the sample vial. The dispense needle can be inserted into the central region of the sample vial to aspirate a portion of the gaseous extracting solvent for analysis. By forming the sample into a thin film, equilibrium occurs much faster and is more uniform than if the sample were in a more conventional shape. Where the sample matrix is a liquid, or some other form which will not maintain the thin film shape after rotation, the rotating operation can be continued while the surface of the sample matrix is washed with a solvent or purged with a gas.

We claim:

1. A method for extracting a component of interest from a sample matrix within a sample vial having a vertical axis comprising the steps of:

forming the sample by placing the sample matrix in the sample vial and rotating the sample vial about the vertical axis at a speed such that centrifugal force causes said sample to form into a thin and uniform layer, wherein the surface area for a given sample volume is maximized; and contacting the thin layer of sample with a solvent for dissolving said component of interest; and removing the solvent containing the component of interest.

2. The method for extracting a desired component of interest as claimed in claim 1, wherein said sample vial is rotated at speed greater than 1000 rpm.

3. A method of thin film extraction within a sample vial having a vertical axis, comprising the steps of:

coating the inside of the sample vial with a thin film of chemically reactive stationary phase; and transporting a liquid sample into said sample vial, forming the liquid sample by rotating the sample vial about the vertical axis at a speed such that centrifugal force causes said liquid sample to form into a thin and uniform layer, wherein the surface area for a given sample volume in contact with the chemically reactive stationary phase is maximized, and the diffusion path to the chemically reactive stationary phase is minimized.

4. The method for thin film extraction within a sample vial as claimed in claim 3, wherein said coating step further comprises the step of rotating the sample vial such that centrifugal force causes the chemically reactive stationary phase to be disposed as a thin film on the inside surface of the sample vial.

5. The method for thin film extraction within a sample vial as claimed in claim 4, further comprising the step of heating the sample vial during rotation to enhance the interaction between the liquid sample and the chemically reactive stationary phase.

6. The method for thin film extraction as claimed in claim 5, wherein said chemically reactive stationary phase further comprises a desiccant coating to retain water from the liquid sample and thereby dry out the sample.

7. The method for thin film extraction as claimed in claim 4, wherein the liquid sample comprises at least a first component and a second component in solution with a first solvent, said method further comprising rotating the sample vial at high speeds to evaporate the first solvent; and introducing a second solvent having the capability of dissolving only the first component but not the second component such that the first component is washed from the walls of the vial and into the second solvent; and removing the second solvent and first component mixture.

8. The method for thin film extraction as claimed in claim 5, further comprising the steps of stopping the rotation of the sample vial such that the liquid sample drains from the inside walls to the bottom of the sample vial.

9. The method for thin film extraction as claimed in claim 8, further comprising the step of aspirating the liquid sample from the bottom of the sample vial for introduction into a chromatograph.

10. The method for thin film extraction as claimed in claim 8, further comprising the step of transporting the sample vial to a detector for sample identification.

11. A method for sample preparation within a sample vial, comprising the steps of:

modifying the inner surface of a sample vial by chemical reaction; and transporting a liquid sample into said sample vial, forming the liquid sample by placing the liquid sample in a sample vial and rotating the sample vial about the vertical axis at a speed such that centrifugal force causes said liquid sample to form into a thin and uniform layer, wherein contact with the modified inner surface is maximized to thereby affect a desired change in the sample; and transporting the liquid sample out of the sample vial.

12. The method for sample preparation as claimed in claim 11, wherein said step of modifying the inner surface further comprises the step of chemically attaching functional groups.

13. A method for sample preparation within a sample vial having a vertical axis, comprising the steps of:

placing a sample matrix containing components of interest within said sample vial; and forming the sample by placing the sample matrix in the sample vial and rotating the sample vial about the vertical axis at a speed such that centrifugal force causes said sample matrix to form into a thin and uniform layer, wherein the surface area for a given sample volume is maximized; and introducing a solvent into said sample vial and rotating said sample vial such that said solvent comes into contact with said sample matrix; and aspirating the headspace containing volatile components of interest from the center of said sample vial.

14. The method for sample preparation within a sample vial as claimed in claim 13, further comprising rotating the sample vial at a speed sufficient to cause the heavier volatilies to be forced away from the center of the sample vial such that the lighter components of interest can be aspirated from the center of the sample vial.

* * * * *